US00PP28380P3

(12) United States Plant Patent
Suphachadiwong

(10) Patent No.: US PP28,380 P3
(45) Date of Patent: Sep. 12, 2017

(54) ***VANDA* PLANT NAMED 'SPCDW1502'**

(50) Latin Name: ***Vanda* spp. Jones ex R. Br.**
Varietal Denomination: SPCDW1502

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 66 days.

(21) Appl. No.: 14/998,795

(22) Filed: Feb. 17, 2016

(65) Prior Publication Data

US 2016/0242344 P1 Aug. 18, 2016

(30) Foreign Application Priority Data

Feb. 17, 2015 (QZ) ..... PBR 2015/0385

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1502' which is characterized by large, prominent sepals and petals with a unique dark blue to purple color, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1502'.

CROSS REFERENCE TO RELATED APPLICATIONS

This application claims priority to the Community Plant Variety Rights application number 2015/0385, filed Feb. 17, 2015, which is herein incorporated by reference.

BACKGROUND OF THE INVENTION

Parentage: The *Vanda* variety 'SPCDW1502' is the result of a planned breeding program. The new variety originated as a seedling from the crossing of the unpatented, proprietary seed parent *Vanda* 'T915' with the unpatented, proprietary pollen parent *Vanda* '370MK'. Both parents were developed by, and are owned by, the inventor and were never commercially released. The crossing was made by the inventor in his research greenhouse in Bangphra, Thailand in February of 2003.

The new variety was first selected in June of 2006, in a research greenhouse in Bangphra, Thailand belonging to the inventor. After identifying the new variety as a potentially interesting selection, the inventor continued confidential testing and propagation of 'SPCDW1502', assessing stability of the unique characteristics of this variety.

Asexual Reproduction: Asexual reproduction of the new cultivar 'SPCDW1502', by way of mericloning, was first initiated in September of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1502' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1502'. These characteristics in combination distinguish 'SPCDW1502' as a new and distinct *Vanda* cultivar:

1. *Vanda* 'SPCDW1502' exhibits a unique dark blue to purple sepal and petal color; and
2. *Vanda* 'SPCDW1502' exhibits large, prominent sepals and petals.

BOTANICAL DESCRIPTION OF THE PLANT

Figure 1:
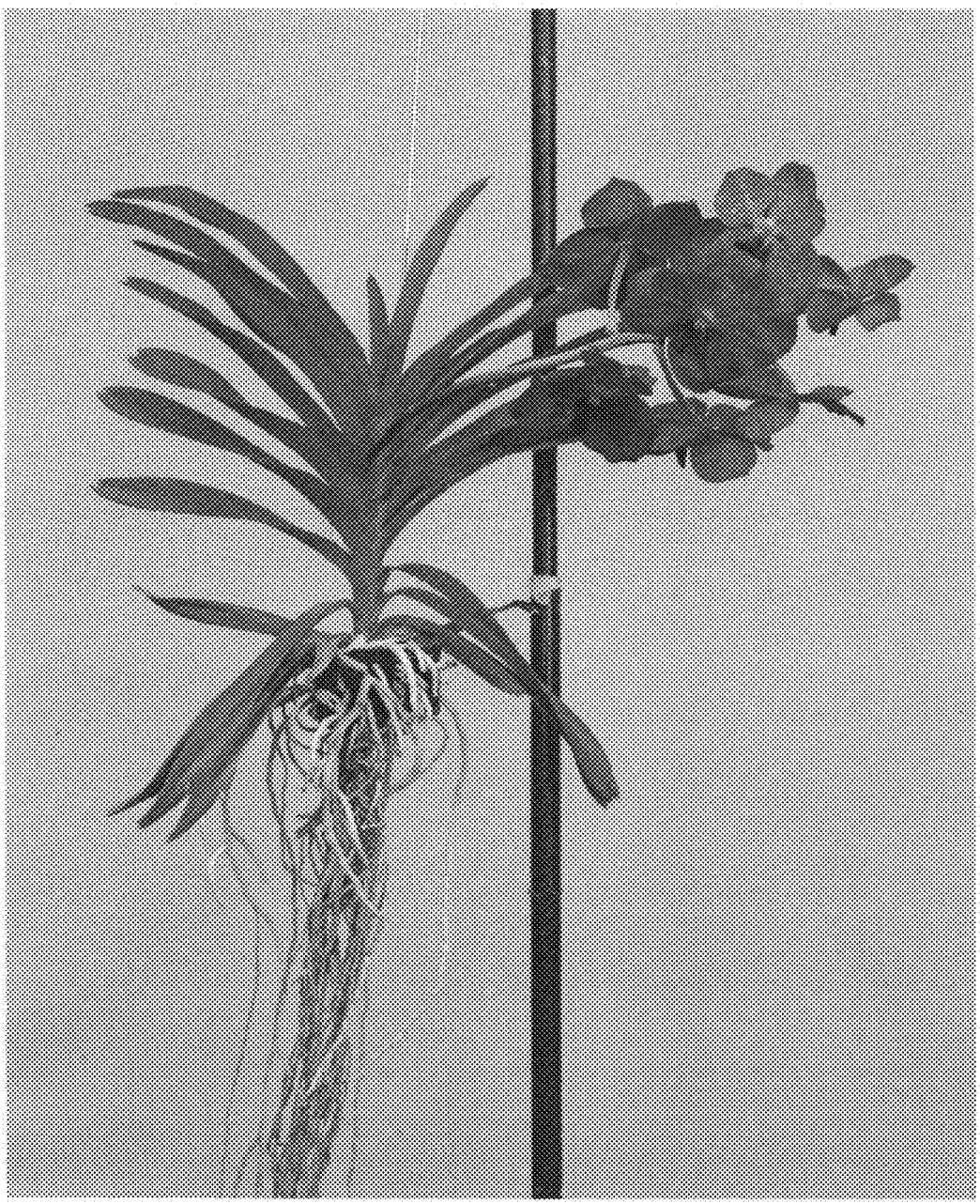
FIG. 1 illustrates, as nearly true as it is reasonably possible to make the same in color photographs of this type, an exemplary plant of 'SPCDW1502' grown in a commercial greenhouse in Honselersdijk, the Netherlands. This plant is approximately 6 years old from the time of mericloning, shown planted in an 8 by 8 cm container.
Figure 2:
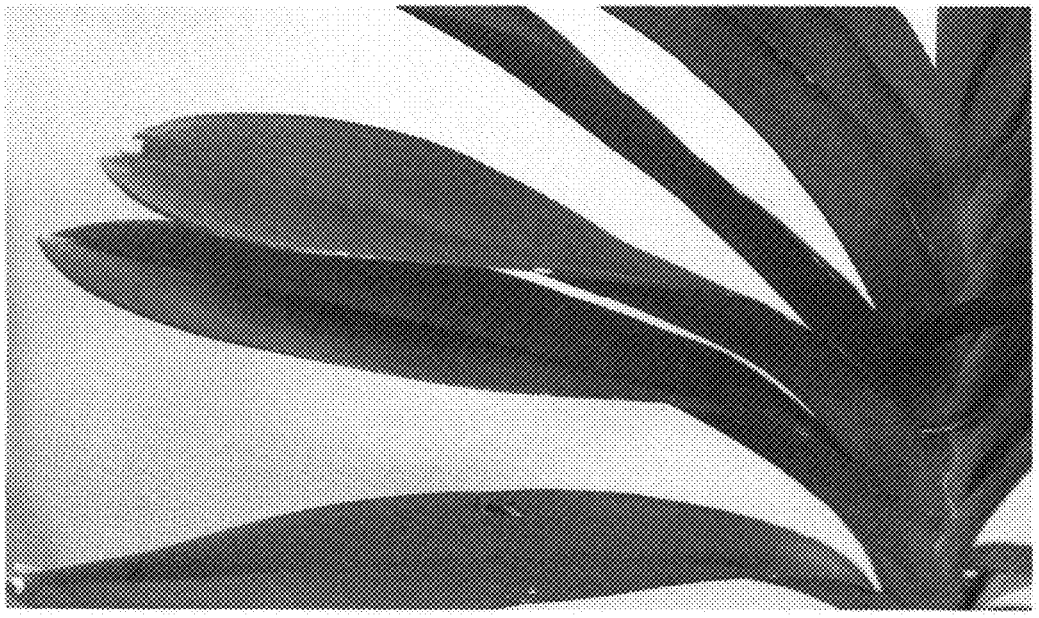
FIG. 2 illustrates, as nearly true as it is reasonably possible to make the same in color photographs of this type, the typical foliage of 'SPCDW1502'.
Figure 3:
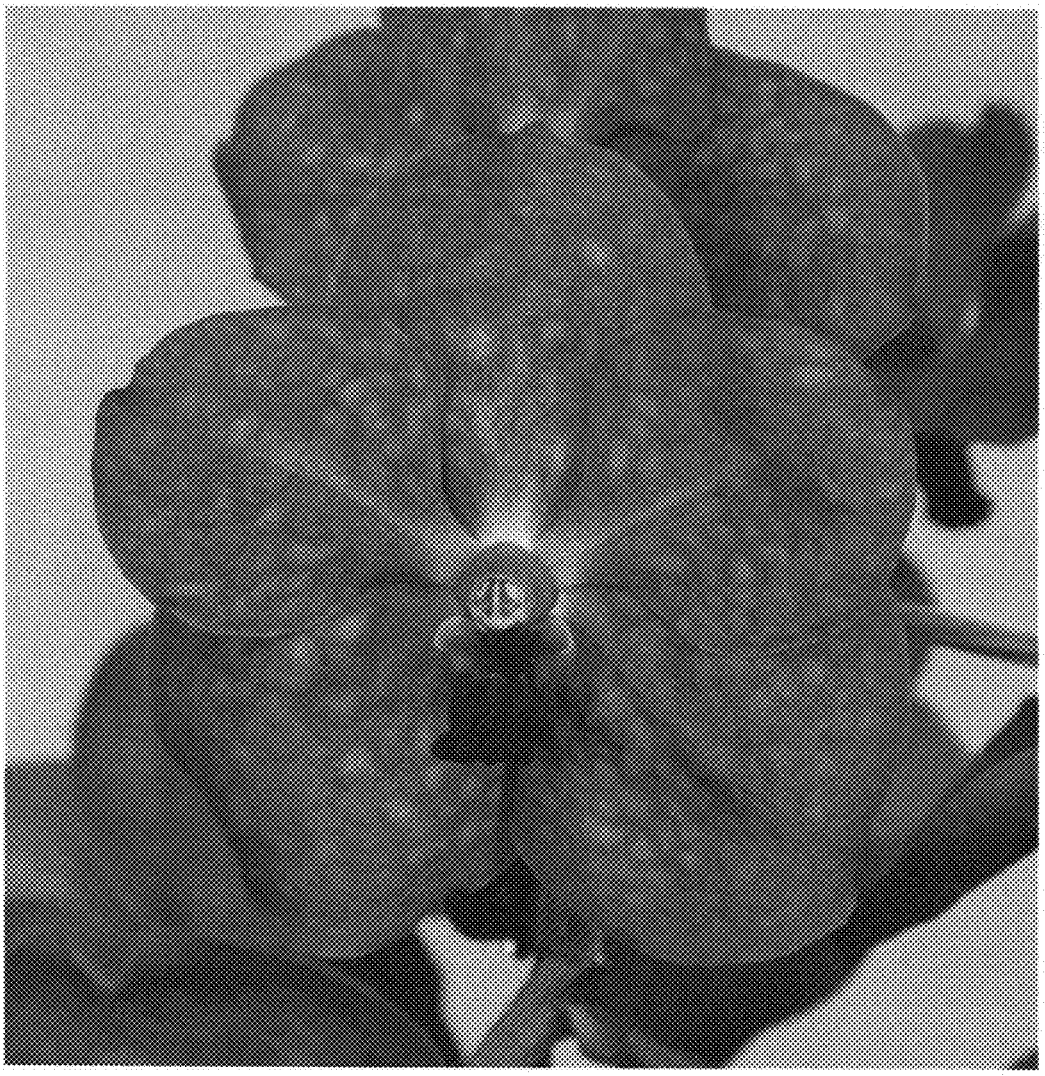
FIG. 3 illustrates, as nearly true as it is reasonably possible to make the same in color photographs of this type, the typical flower of 'SPCDW1502'.
Figure 4:
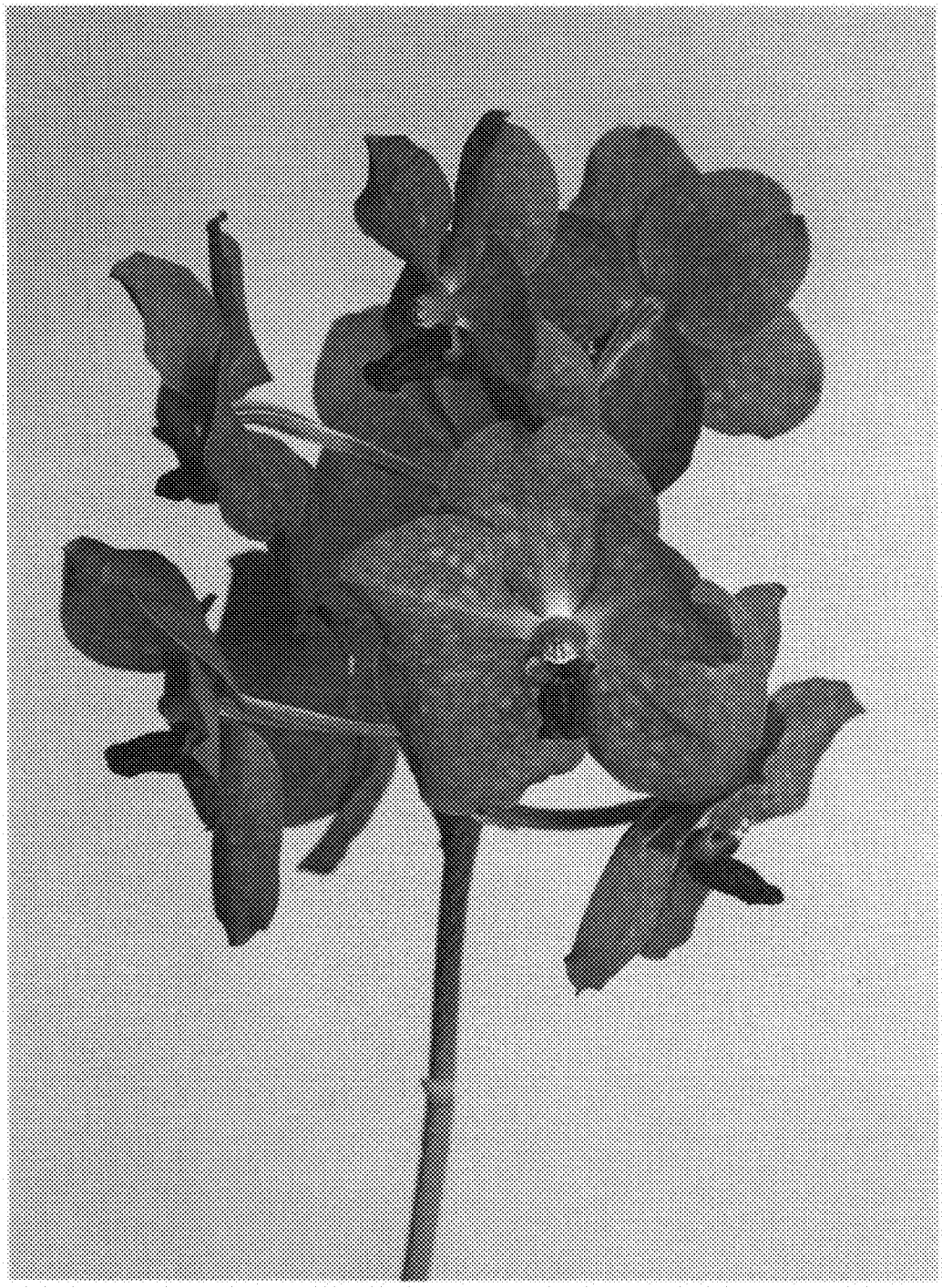
FIG. 4 illustrates, as nearly true as it is reasonably possible to make the same in color photographs of this type, the typical inflorescence of 'SPCDW1502'.

The following observations and measurements made in January of 2016 describe averages from a sample set of six specimens of six year-old 'SPCDW1502' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1502' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1502' and comparisons with other varieties of *Vanda* are provided below.

Plant description:

- *Growth habit.*—Perennial; monopodial, upright. Single monopodial leafy stem, with flowers carried slightly above the leaf plane, inflorescences grow from the leaf axils.
- *Average height from base (plant grown in hanging basket, so no soil line present) to foliar plane.*—31.8 cm.
- *Average height from base (plant grown in hanging basket, so no soil line present) to top of floral plane.*—34.6 cm.
- *Plant spread.*—Average of 41.4 cm.
- *Appropriate container size.*—8 cm by 2 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—53.3 cm long with a diameter of 0.35 cm, on average.
- *Texture.*—Very fleshy; non-fibrous.
- *Color.*—Greyed-Green, near RHS 192C; root apex is yellow-green, RHS 148A.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—14.5 cm.
- *Diameter.*—1.0 cm.
- *Internode length.*—0.4 cm.
- *Luster.*—Matte.
- *Aspect.*—Near vertical.
- *Strength.*—Very strong.
- *Color, juvenile.*—Yellow-green, near RHS 145D.
- *Color, mature.*—Yellow-green, near RHS 145D.
- *Color at internodes.*—Yellow-green, near RHS 145D.
- *Pubescence.*—Glabrous.

Foliage:

- *Arrangement.*—Distichous.
- *Quantity.*—Approximately 25 leaves per plant.
- *Dimensions.*—22.4 cm long and 2.9 cm wide, on average.
- *Shape of blade.*—Ligulate; moderately to strongly carinate.
- *Aspect.*—Slightly to moderately curved.
- *Apex.*—Unequal praemorse.
- *Base.*—Sheathing.
- *Sheath dimensions.*—3.0 cm long and 1.2 cm wide, on average.
- *Sheath color.*—Yellow-green, in between RHS 144B.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and very slightly glossy.
- *Color.*—Juvenile foliage, adaxial surface — Green, near RHS 143B, and darker towards the margins, in between 141B and 143A. Juvenile foliage, abaxial surface — Green, near RHS 143A to 143B. Mature foliage, adaxial surface — Green to yellow-green, in between RHS 143A and 146A, yet slightly darker. Mature foliage, abaxial surface — Green to yellow-green, in between RHS 143B and 146B.
- *Venation.*—Parallel.
- *Venation color, adaxial surface.*—Green to yellow-green, in between RHS 143A and 146A, yet slightly darker.
- *Venation color, abaxial surface.*—Green, RHS 143B to 143C.
- *Petiole.*—No petioles present, leaves sessile.

Inflorescence:

- *Inflorescence arrangement.*—Axially placed raceme.
- *Natural flowering season.*—Autumn into winter.
- *Time to flower.*—Approximately 10 months.
- *Flowers per inflorescence.*—Average of 8; 7 open flowers and 1 bud.
- *Inflorescence height.*—Approximately 21.8 cm (measured from base of lowest flower to top of upper flower).
- *Inflorescence diameter.*—Approximately 19.6 cm.
- *Peduncle.*—Dimensions — Approximately 31.0 cm long and 0.6 cm wide. Aspect — Generally at a 25 degree angle to lateral branch axis; ranging from 20 degrees to 30 degrees to lateral branch axis. Strength — Moderately strong. Texture and luster — Glabrous and moderately glossy. Color — Green, RHS 143B.

Bud:

*Length.*—Average of 1.2 cm.

*Diameter.*—Average horizontal diameter is 1.3 cm; the vertical diameter is 1.6 mm.

*Shape.*—Cubic, with a deltoid apex which is pointed downward.

*Pubescence, texture and luster.*—Glabrous, smooth and moderately glossy.

*Color.*—Yellow-green, near RHS 145A to 145B, and very strongly tinged greyed-purple, near RHS N187A.

Flower:

*Flower type.*—Zygomorphic (orchidaceous), typical shape for the genus *Vanda.*

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 8.9 cm.

*Diameter.*—Approximately 8.9 cm.

*Depth.*—Approximately 3.2 cm.

*Fragrance.*—No fragrance.

*Lastingness.*—3 weeks, on average.

*Persistent.*—Self-cleaning.

*Petals.*—Quantity of Petals — 3 unfused petals; two conventional petals and one labellum. Arrangement — One lateral petal on each side. Length — Approximately 4.6 cm. Width — Approximately 4.1 cm. Shape — Broad ovate to near orbicular. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — Violet-blue, near RHS 90C; veined violet, RHS 85A. Color when opening, lower surface — Violet-blue, near RHS 90B; veined violet, RHS 85A. Color when fully opened, upper surface — Violet, in between RHS 86C and N88B. Color when fully opened, lower surface — Violet, near N88C. Fading, upper surface — Not fading. Fading, lower surface — Not fading. Venation — Reticulate. Venation color, fully opened, upper surface — Violet, in between RHS 86A and N88A; closest to 86A. Venation color, fully opened, lower surface — Violet, in between RHS 86A and N88A; slightly closer to N88A.

*Labellum.*—Shape — Three-lobed, lateral lobes involute, central lobe strongly revolute. Length — Central lobe — Approximately 2.1 cm. Lateral lobes — Approximately 0.9 cm. Width — Central lobe — Approximately 1.1 cm. Lateral lobes — Approximately 0.8 cm. Apex, central lobe — Emarginate. Apex, lateral lobes — Obtuse. Base, central and lateral lobes — Cuneate. Margin, central lobe — Entire; slightly undulate. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte; moderately glossy at the apex. Lateral lobes — Glabrous, velvety, and matte. Color when opening, upper surface — Central lobe — Violet-blue, near RHS N92A; base is slightly lighter, violet to violet-blue, in between RHS 83A and N92A. Lateral lobes — Purple, near RHS N77D; apex is darker, near N77B. Color when opening, lower surface — Central lobe — Violet to violet-blue, in between RHS 83A and N92A, and fading towards the base, near RHS N88D. Lateral lobes — Purple-violet, near RHS N82C; apex is darker, near RHS N82A. Color when fully opened, upper surface — Central lobe — Violet-blue, near RHS N92A; base is slightly lighter, violet to violet-blue, in between RHS 83A and N92A Lateral lobes — Violet, near RHS 86D. Color when fully opened, lower surface — Central lobe — Violet, near RHS 86C, and lighter towards the base, near RHS N87C to N87D; apex is violet-blue, near RHS N92A. Lateral lobes — Violet RHS N88C; apex is violet, near RHS N87B. Fading, upper surface — Not fading. Fading, lower surface — Not fading. Venation — Reticulate. Venation color, fully opened, upper surface — Central lobe — Violet-blue, near RHS N92A; base is slightly lighter, violet to violet-blue, in between RHS 83A and N92A. Lateral lobes — Violet, near RHS 86D. Venation color, fully opened, lower surface — Central lobe — Violet, near RHS 86C, and lighter towards the base, near RHS N87C to N87D; apex is violet-blue, near RHS N92A. Lateral lobes — Violet RHS N88C; apex is violet, near RHS N87B.

*Callosities.*—Dimensions — 1.4 cm long and 0.7 cm wide, on average. Color — Violet, near RHS N87A.

*Spurs.*—Quantity — Average of 1. Length — Approximately 0.5 cm. Diameter — Approximately 0.6 cm. Vertical height — Approximately 0.5 cm, at the base. Shape — Short triangular. Apex — Bluntly acute. Base — Broad Cuneate. Pubescence, texture and luster — Glabrous, smooth, and matte. Color — Violet, near RHS 85D, and striped darker, near N87C to N87D.

*Sepals.*—Quantity — Average of 3 unfused sepals. Arrangement — One dorsal sepal and two lateral sepals. Length — Dorsal sepal — Approximately 4.9 cm. Lateral sepals — Approximately 5.2 cm. Width — Dorsal sepal — Approximately 4.7 cm. Lateral sepals — Approximately 5.8 cm. Shape — Dorsal sepal — Broad ovate. Lateral sepals — Reniform. Apex, dorsal and lateral sepals — Obtuse. Base, dorsal and lateral sepals — Cuneate. Margin, dorsal and lateral sepals — Entire; all sepals are slightly to moderately undulate. Pubescence, texture and luster — Glabrous, velvety, and matte on both the upper and lower sepal surfaces. Color when opening, upper surface — Dorsal sepal — Violet-blue, near RHS 90C; veined violet RHS 85A. Lateral sepals — Greyed-purple, near N187B, and tinged violet-blue, near RHS 90C; veined violet RHS 85A. Color when opening, lower surface — Dorsal sepal — Violet-blue, near RHS 90A to 90B. Lateral sepals — Violet to violet-blue, in between N88B and 90B. Color when fully opened, upper surface —

Dorsal sepal — Violet, in between 86C and N88B. Lateral sepals — Violet, in between 86C and N88B. Color when fully opened, lower surface — Dorsal sepal — Violet, near N88C. Lateral sepals — Violet, near N88C. Fading, upper surface — The color of all sepals does not fade. Fading, lower surface — The color of all sepals does not fade. Venation — Reticulate. Venation color, fully opened, upper surface — Both dorsal and lateral sepals are violet, in between RHS 86A and N88A; slightly closer to RHS 86A. Venation color, fully opened, lower surface — Both dorsal and lateral sepals are violet, in between RHS 86A and N88A; slightly closer to RHS N88A.

*Pedicels.*—Length — Approximately 5.7 cm. Diameter — Approximately 0.4 cm. Angle — Approximately 80 degree angle to peduncle axis. Strength — Moderate. Texture — Glabrous, axially angled with 5 "ribs", axially twisted (due to resupination). Luster — Glossy. Color — Violet, near RHS 83B to 83D; tinged violet-purple, near RHS N82C, at the proximal end.

*Bract.*—Quantity — One bract present at the base of each pedicel. Shape — Broad ovate to reniform; folded around the base of each pedicel. Dimensions — Average of 0.9 cm long and 1.1 cm wide. Apex — Broad acute. Base — Broad Cuneate. Margins — Entire. Color, both surfaces — Yellow-green, near RHS 151B.

Reproductive organs:

*Column.*—Length — Approximately 0.5 cm. Diameter — Approximately 0.7 cm. Color — Violet, in between RHS 83B and 83C.

*Ovary.*—Position — Inferior. Diameter — Approximately 1.1 cm. Color — Purple-violet N181A.

*Pollinia color.*—Yellow-orange RHS 22A.

Seed and fruit: No fruit and seed production has been detected to date.

COMPARISONS WITH THE PARENT PLANTS

Plants of the new cultivar 'SPCDW1502' are similar to the seed parent, *Vanda* 'T915', in most horticultural characteristics. However 'SPCDW1502' differs from the seed parent in the following characteristics:

1. 'SPCDW1502' exhibits a larger plant size compared to 'T915'.
2. The flowers of 'SPCDW1502' are larger than the flowers of 'T915'.
3. The flower color of 'SPCDW1502' is lighter blue compared to the flower color of 'T915'.
4. 'SPCDW1502' exhibits a slower growth rate when compared to 'T915'.

Plants of the new cultivar 'SPCDW1502' are similar to the pollen parent, *Vanda* '370MK', in most horticultural characteristics. However 'SPCDW1502' differs from the pollen parent in the following characteristics:

1. 'SPCDW1502' exhibits narrower foliage than '370MK'.
2. The inflorescence of 'SPCDW1502' is taller than the inflorescence of '370MK'.
3. 'SPCDW1502' is more free-flowering than '370MK'.
4. The flower color of 'SPCDW1502' is darker blue compared to the flower color of '370MK'.

COMPARISON WITH THE MOST SIMILAR *VANDA* CULTIVAR KNOWN TO THE INVENTOR

A comparison of 'SPCDW1502' with the most similar *Vanda* cultivar known to the inventor, *Vanda* 'Princess Mikasa' (not patented), is described in Chart 1.

CHART 1

| Characteristic | 'SPCDW1502' | 'Princess Mikasa' |
|---|---|---|
| Average foliage width | 2.9 cm. | 2.3 cm. |
| Average flower dimensions | Vertical height is 8.9 cm; diameter is 8.9 cm. | Vertical height is 9.3 cm; diameter is 9.2 cm. |
| General coloration of petals when opening | Violet-blue; veined violet. | Violet; lower part of petal finely dotted violet. |
| Length of labellum | Lateral lobes 0.9 cm; central lobe 2.1 cm. | Lateral lobes 0.6 cm; central lobe 1.9 cm. |
| Labellum apices | Lateral lobes obtuse; central lobe emarginate. | Lateral lobes emarginate; central lobe strongly emarginate. |
| Labellum, coloration of central lobe when fully open | Upper surface violet-blue with base slightly lighter, violet to violet-blue; lower surface violet, with lighter violet towards the base and violet-blue at the apex. | Upper surface violet-blue and slightly lighter at the base, violet; lower surface violet and lighter towards the base. |
| Average sepal dimensions | Dorsal sepal is 4.9 cm long and 4.7 cm wide; lateral sepals are 5.2 cm long and 5.8 cm wide. | Dorsal sepal is 4.6 cm long and 4.0 cm wide; lateral sepals are 4.9 cm long and 4.6 cm wide. |
| General coloration of sepals when opening. | Upper surface of lateral sepals are greyed-purple and tinged violet-blue with darker violet reticulate veining. Upper surface of dorsal sepal is violet-blue with darker violet reticulate veining Lower surfaces of all sepals is violet to violet-blue. | All sepals are violet; veins darker. |
| Spur dimensions and shape | 0.5 cm long with a horizontal diameter of 0.6 cm and vertical height of 0.5 cm; short triangular. | 0.8 cm long with a horizontal diameter of 0.25 cm and vertical height of 0.5 cm; flattened, narrow triangular. |

That which is claimed is:

1. A new and distinct variety of *Vanda* plant named 'SPCDW1502', substantially as described and illustrated herein.

* * * * *